US010336668B2

(12) United States Patent
Weidert et al.

(10) Patent No.: US 10,336,668 B2
(45) Date of Patent: Jul. 2, 2019

(54) METHOD FOR PRODUCING CIS- AND TRANS-ENRICHED MDACH

(71) Applicant: BASF SE, Ludwigshafen (DE)

(72) Inventors: Jan-Oliver Weidert, Schifferstadt (DE); Sandra Kramp, Mannheim (DE); Regina Benfer, Altrip (DE); Alexander Panchenko, Ludwigshafen (DE); Andreas Weickgenannt, Mannheim (DE); Norbert Gutfrucht, Lambrecht (DE); Klaus Breuer, Speyer (DE); Artur Kozicki, Bad Duerkheim (DE); Ralph Busch, Worms (DE)

(73) Assignee: BASF SE, Ludwigshafen (DE)

( * ) Notice: Subject to any disclaimer, the term of this patent is extended or adjusted under 35 U.S.C. 154(b) by 85 days.

(21) Appl. No.: 15/529,133

(22) PCT Filed: Nov. 18, 2015

(86) PCT No.: PCT/EP2015/076968
§ 371 (c)(1),
(2) Date: May 24, 2017

(87) PCT Pub. No.: WO2016/083210
PCT Pub. Date: Jun. 2, 2016

(65) Prior Publication Data
US 2017/0260115 A1 Sep. 14, 2017

(30) Foreign Application Priority Data
Nov. 25, 2014 (EP) .................................... 14194717

(51) Int. Cl.
*C07C 7/04* (2006.01)
*B01D 3/00* (2006.01)
(Continued)

(52) U.S. Cl.
CPC ................ *C07C 7/04* (2013.01); *B01D 3/007* (2013.01); *B01D 3/10* (2013.01); *C07C 209/86* (2013.01);
(Continued)

(58) Field of Classification Search
CPC .. C07C 7/04; B01D 3/00; B01D 3/007; B01D 3/10
See application file for complete search history.

(56) References Cited

U.S. PATENT DOCUMENTS 5,736,557 A     4/1998  Hofheinz et al.
5,739,404 A  *  4/1998  Darsow ................. C07C 209/72
                                                          564/450
(Continued)

FOREIGN PATENT DOCUMENTS

DE    101 28 242 A1   12/2002
EP      0 796 839 A1    9/1997
(Continued)

OTHER PUBLICATIONS

European Search Report dated Aug. 5, 2015 in Patent Application No. 14194717.6 (with English translation of categories of cited documents).
(Continued)

Primary Examiner — Brian A McCaig
(74) Attorney, Agent, or Firm — Oblon, McClelland, Maier & Neustadt, L.L.P.

(57) ABSTRACT

A process for preparing trans-enriched MDACH, including: distilling an MDACH starting mixture in the presence of an auxiliary, which is an organic compound having a molar mass of 62 to 500 g/mol, a boiling point at least 5° C. above the boiling point of cis,cis-2,6-diamino-1-methylcyclohexane, and 2 to 4 functional groups, each of which is independently an alcohol group or a primary, secondary or
(Continued)

(DISTILLATION 1):

tertiary amino group. The MDACH starting mixture includes 0 to 100% by weight of 2,4-MDACH and 0 to 100% by weight of 2,6-MDACH, based on the total amount of MDACH present in the MDACH starting mixture. The MDACH starting mixture includes both trans and cis isomers. Trans-enriched MDACH includes 0 to 100% by weight of 2,4-MDACH and 0 to 100% by weight of 2,6-MDACH, where the proportion of trans isomers in the mixture is higher than the proportion of trans isomers in the MDACH starting mixture.

26 Claims, 3 Drawing Sheets

(51) Int. Cl.
*B01D 3/10* (2006.01)
*C07C 209/86* (2006.01)
*C07C 211/36* (2006.01)

(52) U.S. Cl.
CPC ........ *C07C 211/36* (2013.01); *C07C 2601/14* (2017.05)

(56) References Cited

U.S. PATENT DOCUMENTS

2004/0199033 A1   10/2004  Bottcher et al.
2012/0226017 A1*  9/2012   Pfeffinger ............... C08L 63/00
                                                              528/405

FOREIGN PATENT DOCUMENTS

WO          95/35287 A1     12/1995
WO          2011/032677 A1   3/2011
WO          2011/033104 A1   3/2011

OTHER PUBLICATIONS

International Preliminary Report on Patentability dated Aug. 2, 2017 in PCT/EP2015/076968 filed Nov. 18, 2015 (with English translation).
International Search Report dated Jan. 26, 2016 in PCT/EP2015/076968 (English translation previously filed).
International Search Report dated Jan. 26, 2016 in PCT/EP2015/076968 filed Nov. 18, 2015.

* cited by examiner

Figure 1 (DISTILLATION 1):
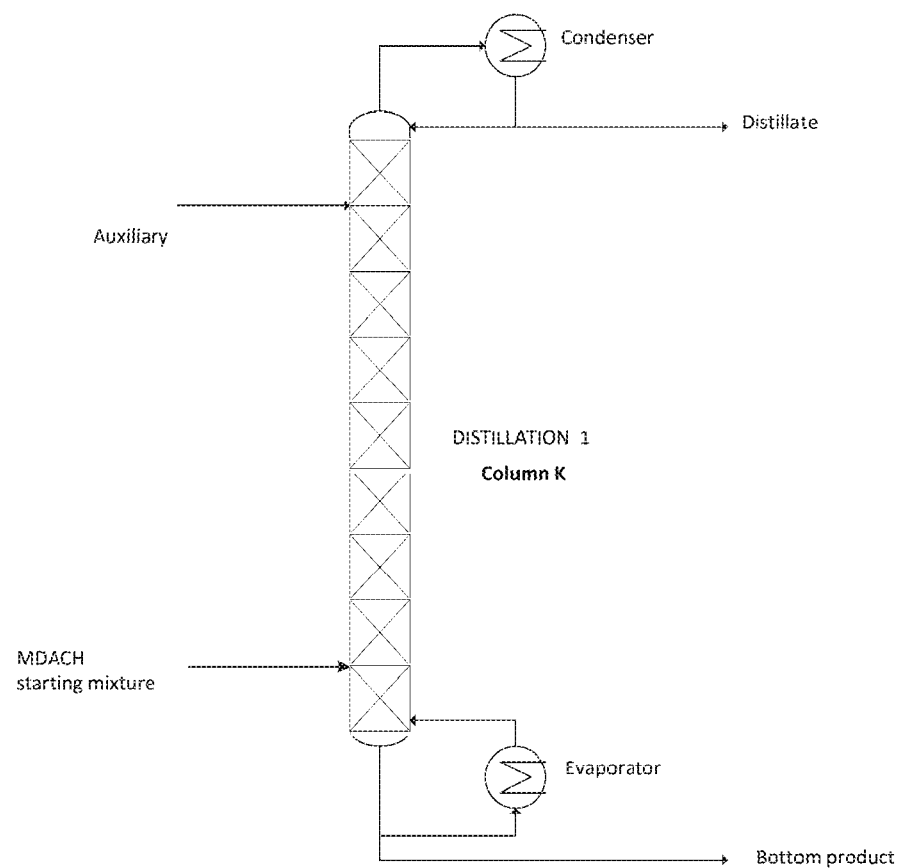

Figure 2 (DISTILLATIONS 1 and 2):
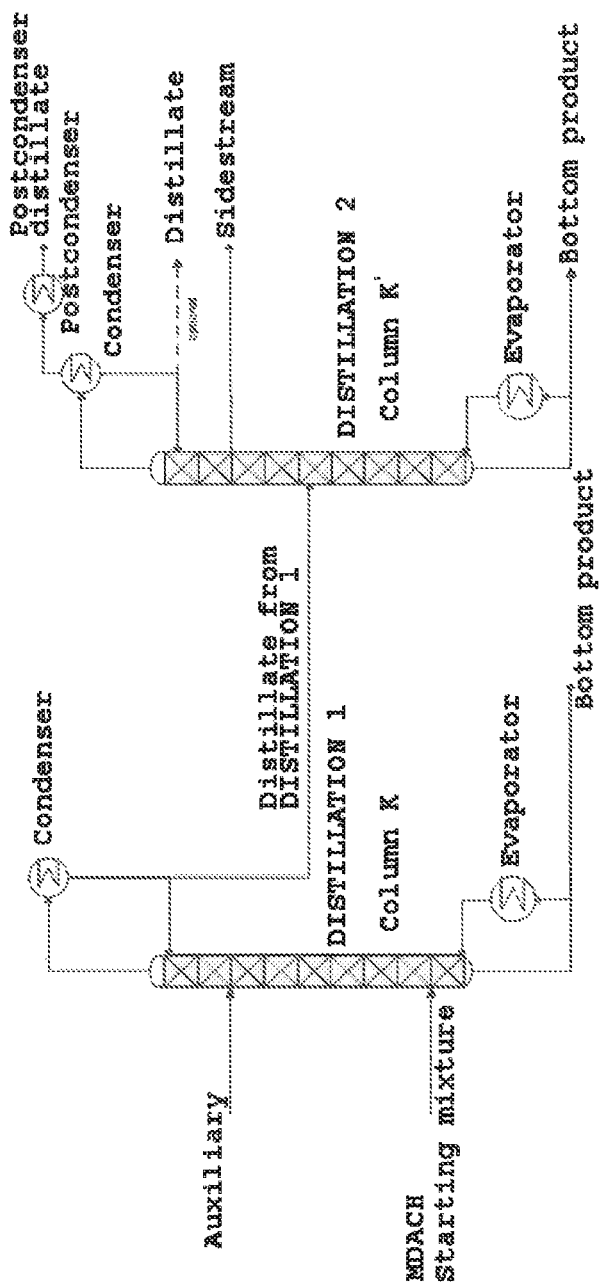

Figure 3 (preparation of cis-enriched MDACH and recovery of the auxiliary):
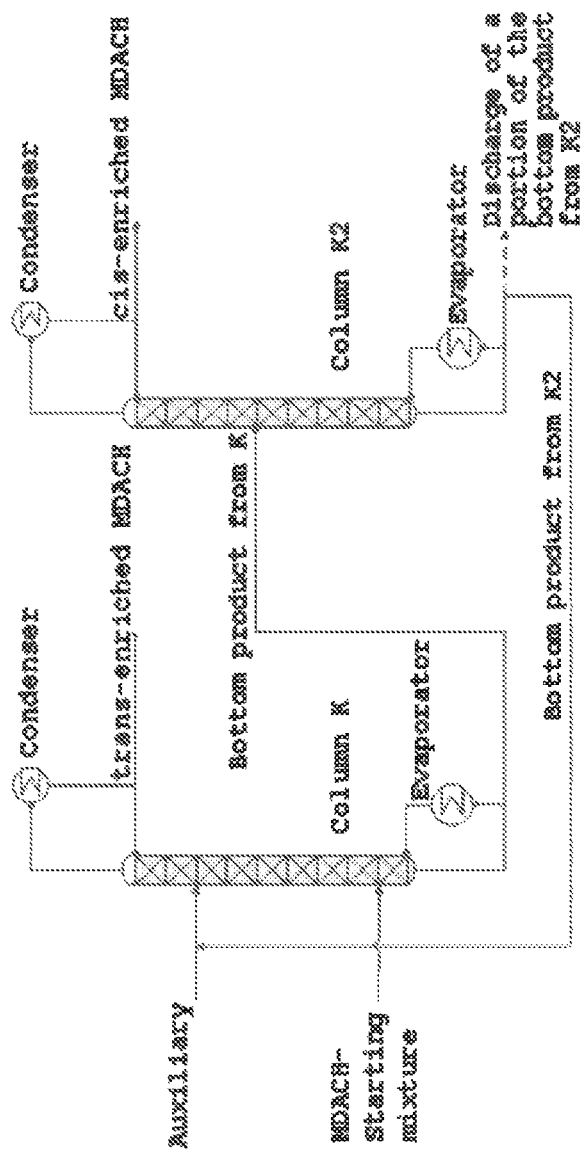

METHOD FOR PRODUCING CIS- AND TRANS-ENRICHED MDACH

BACKGROUND OF THE INVENTION

Field of the Invention

The subject matter of the present invention relates to a process for preparing trans-enriched MDACH. The invention further relates to a process for preparing cis- and trans-enriched MDACH. The invention likewise relates to cis- and trans-enriched MDACH.

The distillative separation of cis and trans isomers of a mixture of 2,4-diamino-1-methylcyclohexane (2,4-MDACH) and 2,6-diamino-1-methylcyclohexane (2,6-MDACH) is possible only with very great difficulty because of the closeness of the boiling points to one another.

Description of the Related Art

EP 0 796 839 A1 (Bayer AG) describes the continuous preparation of a mixture of aminomethyl-cyclohexanes and diaminomethylcyclohexanes by catalytic hydrogenation of diaminotoluenes with hydrogen. Further described is the distillative separation of the resultant aminomethyl-cyclohexanes and diaminomethylcyclohexanes. There is no teaching of any additional distillation step for enrichment of cis or trans isomers.

WO 2011/033104 A1 (BASF SE) relates inter alia to mixtures comprising the 7 stereoisomers of diaminomethylcyclohexane in very specific ratios to one another. The mixtures are prepared by hydrogenating toluenediamine, wherein the resultant hydrogenation product is purified by distillation. Here too, there is no teaching of any additional distillation step for enrichment of cis or trans isomers.

For the further reaction of 2,4- and 2,6-MDACH to give corresponding conversion products it may be advantageous to use mixtures having an elevated proportion of trans isomers. It may likewise be advantageous to use mixtures having an elevated proportion of cis isomers.

SUMMARY OF THE INVENTION

It was therefore an object of the present invention to provide mixtures of 2,4- and 2,6 MDACH having an elevated proportion of trans isomers. In addition, corresponding mixtures having an elevated proportion of cis isomers were to be provided. More particularly, a process with which mixtures of this kind can be prepared was to be found.

The object is achieved by a process for preparing trans-enriched MDACH, which comprises conducting the distillation of an MDACH starting mixture in the presence of an auxiliary, wherein trans-enriched MDACH is distilled off, and wherein the auxiliary is an organic compound having
a molar mass of 62 to 500 g/mol,
a boiling point at least 5° C. above the boiling point of cis,cis-2,6-diamino-1-methylcyclohexane, where the boiling points are each based on a pressure of 50 mbar, and
2 to 4 functional groups, each of which is independently an alcohol group or a primary, secondary or tertiary amino group,
the MDACH starting mixture comprises 0% to 100% by weight of 2,4-diamino-1-methylcyclohexane (2,4-MDACH) and 0% to 100% by weight of 2,6-diamino-1-methylcyclohexane (2,6-MDACH), based on the total amount of MDACH (=2,4- and 2,6-MDACH) present in the MDACH starting mixture, and
wherein the MDACH starting mixture comprises both trans and cis isomers,
and
trans-enriched MDACH is a mixture comprising 0% to 100% by weight of 2,4-MDACH and 0% to 100% by weight of 2,6-MDACH, based on the total amount of MDACH present in the mixture, where the proportion of trans isomers in the mixture, based on the total amount of MDACH present in the mixture, is higher than the proportion of trans isomers in the MDACH starting mixture, based on the amount of MDACH present in the MDACH starting mixture.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1: The column (K) is equipped with an evaporator and a condenser. The MDACH starting mixture is fed in continuously in the lower third and the auxiliary in the upper third of the theoretical plates of the column (steps a) and b)), The distillate drawn off is trans-enriched MDACH (step c)).

FIG. 2: The columns (K and K') have been provided with an evaporator and a top condenser. The top condenser of K' is followed downstream by a postcondenser. The MDACH starting mixture is fed in continuously in the lower third and the auxiliary in the upper third of the theoretical plates of the first column (K) (steps a) and b)). As distillate, trans-enriched MDACH is drawn off (step c)). This distillate is fed to a second column (K') (step d)). In the postcondenser, postcondenser distillate is drawn off. Optionally, distillate can likewise be drawn off in the top condenser. Trans-enriched MDACH is drawn off in the sidestream (step e)).

FIG. 3: The auxiliary is fed in in the upper third and the MDACH starting mixture in the lower third of the theoretical plates of K (steps I a) and I b)). Trans-enriched MDACH is withdrawn as distillate (step I c)). The bottom product from K is fed to a second column (K2) (step II a)). As distillate, cis-enriched MDACH is drawn off from K2 (step II b)). The bottom product from K2 is recycled into K (step III). A portion of the bottom product from K2 is discharged.

DETAILED DESCRIPTION OF THE PREFERRED EMBODIMENTS

It has been recognized in accordance with the invention that cis and trans isomers of 2,4-MDACH and 2,6-MDACH can be better separated from one another by virtue of the presence of the auxiliary of the invention.

The auxiliary is an organic compound. This is understood to mean a molecular compound in which carbon is present in conjunction with hydrogen. For example, the compound may be an aliphatic compound. The term "aliphatic compound" refers to an organic compound having no aromatic ring system. An aliphatic compound may be branched or unbranched and may comprise any functional groups or heteroatoms. The term "aliphatic compounds" also comprises cyclic aliphatic (cycloaliphatic) compounds. In a cycloaliphatic compound, at least some of the atoms that form the compound are joined to one another in the molecule so as to form one or more rings.

The compound may likewise also be an organic compound comprising an aromatic ring system, especially a tolyl or phenyl radical:

A functional group in the context of the present invention is an alcohol group or a primary, secondary or tertiary amino group.

For trans-enriched MDACH to be obtained overhead, the majority of the auxiliary should remain in the bottoms during the distillation or, in the case of a continuous reaction regime, be drawn off via the bottom. The boiling point of the auxiliary must therefore be at least 5° C. above the boiling point of cis,cis-2,6-diamino-1-methylcyclohexane, where the boiling points are each based on a pressure of 50 mbar. This means that both the boiling point of the auxiliary and the boiling point of the cis,cis-2,6-diamino-1-methylcyclohexane, which has the highest boiling point of all the isomers of 2,4- and 2,6-MDACH, is determined at 50 mbar. The boiling point of the auxiliary is preferably higher by 5 to 100° C. more preferably 10 to 50° C. and most preferably 20 to 30° C. than that of cis,cis-2,6-diamino-1-methylcyclohexane. Given a correspondingly high boiling point of the auxiliary, the bottoms have to be more strongly heated during the distillation, which promotes the breakdown of the MDACH, in this respect, the upper limit in the preferred ranges is correspondingly lower.

In a particularly preferred embodiment, the abovementioned boiling points are based not on 50 mbar but on the top pressure at which the distillation of the MDACH starting mixture is effected. If the distillation is to be effected for example, at a top pressure of 40 mbar, this can be correspondingly established by the person skilled in the art, for example with the aid of a vacuum pump. The person skilled in the art here will choose an auxiliary having a boiling point at said pressure of 40 mbar which is at least 5° C. or 5 to 100° C., 10 to 50° C. or 20 to 30° C. above the boiling point, in that case likewise determined at 40° C., of cis,cis-2,6-diamino-1-methylcyclohexane.

In this particularly preferred embodiment, the auxiliary consequently has boiling point at least 5° C., preferably 5 to 100° C., more preferably 10 to 50° C. and most preferably 20 to 30° C. above the boiling point of cis,cis-2,6-diamino-1-methylcyclohexane, where the boiling points are each based on the top pressure at which the distillation of the MDACH starting mixture takes place. The boiling points of the isomers of MDACH are very close to one another. If, at a particular pressure, cis,cis-2,6-diamino-1-methylcyclohexane should not have the greatest boiling point, the differences in the boiling points of the auxiliary and of the isomers of 2,4- and 2,6-MDACH present in the MDACH starting mixture are therefore always in the order of magnitude of at least 5° C. There will therefore be sufficient separability of auxiliary and MDACH.

Useful auxiliaries in principle are those which form a high-boiler azeotrope With the cis isomers of MDACH.

Preference is given to using those auxiliaries which, at a pressure of 1 bar, have a melting point of less than 60° C., preferably less than 10° C., more preferably less than 0° C. and most preferably less than −5° C. A low melting point has the advantage that the auxiliary is in liquid form under the typical distillation conditions and does not first have to be melted. Especially with regard to a continuous process, such auxiliaries have the further advantage that the auxiliary does not solidify again in the pipelines of the plant. This would otherwise have to be prevented by heating the pipelines, which would lead to higher running and fixed costs.

The molar mass of the auxiliary is from 62 to 500 g/mol, preferably 75 to 400 g/mol, more perferably 76 to 300 g/mol and most preferably 100 to 250 g/mol or even 120 to 200 g/mol.

Preferably, the auxiliary, aside from the functional groups, has no further heteroatoms or 1 to 3 ether group(s), and otherwise, aside from the functional groups, no further heteroatoms. The term "heteroatom" is understood to mean those atoms that are not carbon or hydrogen. The auxiliary preferably has 1 to 2 or even one ether group(s) and otherwise, aside from the functional groups, no further heteroatoms. The auxiliary likewise preferably, aside from the functional groups, has no further heteroatoms. Preference is given in this context, for example, to alkanols and cycloalkanols, especially alkanols. Examples of auxiliaries comprising ether groups include diethylene glycol, triethylene glycol, dipropylene glycol or 4-(2-hydroxethyl) morpholine.

Preferably, the auxiliary has either
  2 to 4, preferably 2 to 3 and more preferably two alcohol groups,
  a primary, secondary or tertiary amino group and 1 to 3 or 1 to 2 or exactly one alcohol group(s), or
  2 to 4, preferably 2 to 3 and more preferably two functional groups, each of which is independently a primary, secondary or tertiary amino group.

More preferably, the auxiliary has either
  2 to 4, preferably 2 to 3 and more preferably two alcohol groups, or
  a primary, secondary or tertiary amino group and 1 to 3 or 1 to 2 or exactly one alcohol group(s).

Preferably, in the auxiliary, at least two of the functional groups or, in the case that the auxiliary has exactly two functional groups, the two functional groups are in 1,2, 1,3, 1,4 or 1,5 positions to one another. This should be understood to mean the relative position of the functional groups to one another. In the context of the present invention, for example, both propane-1,3-diol and pentane-2,4-diol are a 1,3-diol. More preferably, in the auxiliary, at least two of the functional groups or, in the case that the auxiliary has exactly two functional groups, the two functional groups are in 1,2, 1,3 or 1,4 positions to one another.

A good separation can be achieved inter alia when the auxiliary has two to four alcohol groups.

In an embodiment which is preferred in this context, the auxiliary is an organic compound having
  a molar mass of 62 to 250 g/mol,
  a boiling point at least 5° C. above the boiling point of cis,cis-2,6-diamino-1-methylcyclohexane, where the boiling points are each based on a pressure of 50 mbar,
  a melting point of less than 60° C. at a pressure of 1 bar, and
  2 to 4 alcohol groups,
  where the auxiliary, aside from the alcohol groups, has no further heteroatoms or one or two ether groups and otherwise, aside from the alcohol groups, has no further heteroatoms.

The statements made above with regard to the boiling and melting, points likewise apply to this embodiment.

The molar mass of this organic compound is preferably 76 to 200 g/mol, more preferably 90 to 170 g/mol and most preferably 90 to 100 g/mol.

Further preferably, the compound here is an aliphatic compound which may either be saturated or unsaturated and is more preferably acyclic.

Most preferably, an auxiliary of this kind is a compound having two or three alcohol groups or even a compound having exactly two alcohol groups, i.e. a diol.

More preferably, at least two of the alcohol groups here or, in the case that the auxiliary has exactly two alcohol groups, the two alcohol groups are in 1,3 or 1,4 positions to one another.

An example of a compound having four OH groups is diglycerol. Triols (compounds having three OH groups) for use with preference are, for example, glycerol, trimethylolpropane, hexane-1,3,6-triol, and hexane-1,2,6-triol.

More preferably, the auxiliary is a diol, especially an aliphatic diol. Particularly preferred diols are alkanediols or cycloalkanediols. Particular preference is given here to the $C_3$- to $C_{10}$-alkanediols, very particular preference to the $C_3$- to $C_6$-alkanediols. The alkanediols are preferably unbranched.

Suitable diols are, for example, butane-1,4-diol, butene-1,4-diol, but also ethers derived from ethylene glycol, for example diethylene glycol or triethylene glycol.

Preferably, the auxiliary is a 1,2-diol, especially an aliphatic 1,2-diol, a 1,2-diol being understood to mean a compound in which the OH groups are in vicinal positions to one another. Particularly preferred 1,2-diols are alkane-1,2-diols or cycloalkane-1,2-diols. Particular preference is given here to the $C_4$- to $C_{10}$-alkane-1,2-diols, very particular preference to the $C_4$- to $C_6$-alkane-1,2-diols. The alkane-1, 2-diols are preferably unbranched.

Suitable cyclic 1,2-diols are, for example, cyclohexane-1,2-diol and cyclohexane-1,2-dimethanol. Suitable alkane-1,2-diols are, for example, hexane-1,2-diol and pentane-1, 2-diol.

A very particularly good separation can be achieved when the OH groups of the auxiliary are in 1,3 positions to one another. Preferably, the auxiliary is therefore a 1,3-diol, especially an aliphatic 1,3-diol. Particularly preferred 1,3-diols are alkane-1,3-diols or cycloalkane-1,3-diols, Particular preference is given here to the $C_3$- to $C_{10}$-alkane-1,3-diols, very particular preference to the $C_3$- to $C_6$-alkane-1, 3-diols. The alkane-1,3-diols are preferably unbranched.

Suitable branched alkane-1,3-diols are, for example, 2-methylpropane-1,3-diol or neopentyl glycol. Suitable unbranched alkane-1,3-diols are, for example, propane-1,3-diol, butane-1,3-diol, pentane-1,3-diol, pentane-2,4-diol, hexane-1,3-diol and hexane-2,4-diol.

Particular preference is given to diols which are a $C_3$-$C_{10}$-alkane-1,3-diol or a $C_4$-$C_{10}$-alkane-1,4-diol.

A good separation can also be achieved when the auxiliary is a primary, secondary, or tertiary amino group and comprises 1 to 3 alcohol group(s), i.e. it is an amino alcohol. Suitable amino alcohols are, for example, diethanolamine and triethanolamine. An example of an amino alcohol which is suitable in this context is 1,3-aminopropanol.

In an embodiment which is preferred in this context, the auxiliary is an organic compound having
a molar mass of 75 to 300 g/mol,
a boiling point at least 5° C. above the boiling point of cis,cis-2,6-diamino-1-methylcyclohexane, where the boiling points are each based on a pressure of 50 mbar,
a melting point of less than 60° C. at a pressure of 1 bar, and
a primary, secondary or tertiary amino group and 1 to 3 alcohol group(s),
where the auxiliary, aside from the alcohol groups, has no further heteroatoms or one ether group and otherwise, aside from the functional groups, has no further heteroatoms.

A functional group in the context of this embodiment is an alcohol group or a primary, secondary or tertiary amino group.

The statements made above with regard to the boiling and melting points likewise apply to this embodiment.

An auxiliary of this kind has a primary, secondary or tertiary amino group and 1 to 3, 1 to 2 or one alcohol group(s).

The molar mass of this organic compound is preferably 100 to 250 g/mol, more preferably 110 to 200 g/mol and most preferably 115 to 180 g/mol.

An auxiliary of this kind is preferably an aliphatic compound, especially a saturated aliphatic compound. Useful compounds here include both cyclic and acyclic compounds. The compound may likewise also be an organic compound comprising an aromatic ring system, specially a tolyl or phenyl radical.

A good separation can likewise be achieved when the auxiliary has 2 to 4 functional groups which are each independently a primary secondary or tertiary amino group.

In an embodiment which is preferred in this context, the auxiliary is an organic compound having
a molar mass of 100 to 300 g/mol,
a boiling point at least 5° C. above the boiling point of cis,cis-2,6-diamino-1-methylcyclohexane, where the boiling points are each based on a pressure of 50 mbar,
a melting point of less than 60° C. at a pressure of 1 bar, and
2 to 4 functional groups, each of which is independently a primary, secondary or tertiary amino group,
where the auxiliary, aside from the functional groups, has no further heteroatoms.

A functional group in the context of his embodiment is understood to mean a primary, secondary or tertiary amino group.

The statements made above with regard to the boiling and melting points likewise apply to this embodiment.

The molar mass of this organic compound is preferably 120 to 250 g/mol, more preferably 150 to 200 g/mol of and most preferably 150 to 180 g/mol.

An auxiliary of this kind has preferably 2 to 3 and more preferably two functional groups, which are independently a primary, secondary or tertiary amino group.

Preferably, an auxiliary of this kind here is an aliphatic, especially cycloaliphatic, compound which is preferably saturated.

Suitable auxiliaries include the following compounds:
ethylene glycol propane-1,2-diol, 2-methylpropane-1,3-diol, butane-1,2-diol, butane-2,3-diol, 2-methylbutane-1,2-diol, 3-methylbutane-1,2-diol, 3-methylbutane-1,3-diol, pentane-1,2-diol, pentane-1,3-diol, pentane-2,4-diol, pentane-2,3-diol, hexane-1,2-diol, cis-cyclopentane-1,2-diol, trans-cyclopentane-1,2-diol, cis-cyclohexane-1,2-diol, trans-cyclohexane-1,2-diol, propane-1,3-diol, 2-methylpropane-1,3-diol, 2,2-dimethylpropane-1,3-diol (neopentyl glycol), butane-1,3-diol, pentane-1,2-diol, pentane-2,4-diol, pentane-1,5-diol, hexane-1,3-diol, hexane-2,4-diol, cyclobutane-1,3-diol, cyclopentane-1,3-diol, cyclohexane-1,3-diol, cis- and trans-butene-1,4-diol, butane-1,4-diol, 2,3-dimethylbutane-1,4-diol, 2,2-dimethylbutane-1,4-diol, pentane-1,4-diol, 2,3-dimethylpentane-1,5-diol, hexane-1,4-diol, cyclohexane-1,4-diol, hexane-1,3,6-triol, hexane-1,2, 3-triol, hexane-1,2,6-triol, glycerol, diglycerol, sorbitol, pentaerythritol, diethylene glycol, triethylene glycol, dipropylene glycol;
diethanolamine, N-methyldiethanolamine, N-propyldiethanolamine, N-butyldiethanolamine, triethanolamine N-ethylpropanolamine, N-propylethanolamine, N,N-dipropylethanolamine, N-butylethanolamine, N,N-dibutylethanolamine, propanolamine, dipropanolamine, N-methyldipropanolamine, N-propyldipropanolamine, N-butyldipropanolamine, tripropanolamine, diisopropanolamine, N-methyldiisopropanolamine, triisopropanolamine, N-2-methylaminopropanol, 4-amino-1-butanol, 4-(2-hydroxyethyl)morpholine, pentanolamine, hydroxyethylpiperazine, N-(2-hydroxyethyl)aniline, N,N-di(2-hydroxyethyl)aniline, 3-amino-1-propanol;

2-(diisopropylamino)ethylamine, 3-(cyclohexylamino)propylamine, dipropylenetriamine, triethylenetetramine, pentamethyldiethylenetriamine, 3-(2-aminoethylamino)propylamine, diethylenetriamine, isophoronediamine.

Preferred auxiliaries are the following compounds:

ethylene glycol, propane-1,2-diol, 2-methylpropane-1,3-diol, butane-1,2-diol, butane-2,3-diol, 2-methylbutane-1,2-diol, 3-methylbutane-1,2-diol, 3-methylbutane-1,3-diol, pentane-1,2-diol, pentane-1,3-diol, pentane-2,4-diol, pentane-2,3-diol, hexane-1,2-diol, cis-cyclopentane-1,2-diol, trans-cyclopentane-1,2-diol, propane-1,3-diol, pentane-1,5-diol, 2-methylpropane-1,3-diol, butane-1,3-diol, pentane-1,2-diol, pentane-2,4-diol, hexane-1,3-diol, hexane-2,4-diol, cyclobutane-1,3-diol, cyclopentane-1,3-diol, cyclohexane-1,3-diol, cis- and trans-butene-1,4-diol, butane-1,4-diol, 2,3-dimethylbutane-1,4-diol, 2,2-dimethylbutane-1,4-diol, pentane-1,4-diol. 2,3-dimethylpentane-1,5-diol, hexane-1,4-diol, hexane-1,3,6-triol, hexane-1,2,6-triol, glycerol, diglycerol, diethylene glycol, triethylene glycol, dipropylene glycol;

diethanolamine, N-methyldiethanolamine, N-propyldiethanolamine, N-butyldiethanolamine, triethanolamine, N-ethylpropanolamine, N-propylethanolamine, N,N-dipropylethanolamine, N-butylethanolamine, N,N-dibutylethanolamine, propanolamine, dipropanolamine, N-methyldipropanolamine, N-propyldipropanolamine, N-butyldipropanolamine, tripropanolamine, diisopropanolamine, N-methyldiisopropanolamine, triisopropanolamine N-2-methylaminopropanol, 4-amino-1-butanol, 4-(2-hydroxyethyl)morpholine, pentanolamine, hydroxyethylpiperazine, N-(2-hydroxyethyl)aniline, N,N-di(2-hydroxyethyl)aniline, 3-amino-1-propanol;

2 (diisopropylamino)ethylamine, 3-(cyclohexylamino)propylamine, dipropylenetriamine, triethylenetetramine, pentamethyldiethylenetriamine, 3-(2-aminoethylamino)propylamine, diethylenetriamine, isophoronediamine.

Particular preference is given to the following auxiliaries:

2-methylpropane-1,3-diol, hexane-1,2-diol, cis-cyclopentane-1,2-diol, trans-cyclopentane-1,2-diol, propane-1,3-diol, pentane-1,5-diol, 2-methyl-propane-1,3-diol, hexane-1,3-diol, hexane-2,4-diol, cyclobutane-1,3-diol, cyclopentane-1,3-diol, cyclohexane-1,3-dial, cis- and trans-butene-1,4-diol, butane-1,4-diol, 2,3-dimethylbutane-1,4-diol, 2,2-dimethylbutane-1,4-diol, pentane-1,4-diol, 2,3-dimethylpentane-1,5-diol, hexane-1,4-diol, hexane-1,3,6-triol, hexane-1,2,6-triol, glycerol, diglycerol, diethylene glycol, triethylene glycol, dipropylene glycol;

diethanolamine, N-methyldiethanolamine, N-propyldiethanolamine, N-butyldiethanolamine, triethanolamine, N-ethylpropanolamine, N-propylethanolamine, N,N-dipropylethanolamine, N,N-dibutylethanolamine, dipropanolamine, N-methyldipropanolamine, N-propyldipropanolamine, N-butyldipropanolamine, tripropanolamine, diisopropanolamine, N-methyldiisopropanolamine, triisopropanolamine, N-2-methylaminopropanol, 4-(2-hydroxyethyl)morpholine, pentanolamine, hydroxyethylpiperazine, N-(2-hydroxyethyl)aniline, N,N-di(2-hydroxyethyl)aniline;

3-(cyclohexylamino)propylamine, dipropylenetriamine, triethylenetetramine, 2-aminoethylamino) propylamine, isophoronediamine.

Very particular preference is given to glycerol, propane-1,3-diol, butane-1,4-diol, cis-butene-1,4-diol, triethylene glycol, diglycerol, pentane-1,5-diol, 4 (2-hydroxyethyl)morpholine, N-(2-hydroxyethyl) aniline, triethanolamine, N-methyldiethanolamine.

Very particular preference is given especially to propane-1,3-diol and butane-1,4-diol.

The MDACH starting mixture comprises 0% to 100% by weight of 2,4-diamino-1-methyl-cyclohexane (2,4-MDACH) and 0% to 100% by weight of 2,6-diamino-1-methylcyclohexane (2,6-MDACH), based on the total amount of MDACH present in the MDACH starting mixture (=2,4- and 2,6-MDACH). In addition, the MDACH starting mixture comprises both trans and cis isomers.

The MDACH starting mixture may also comprise further isomers of diamino-1-methylcyclo-hexane, particularly vicinal diamino-1-methylcyclohexane compounds, for example 2,3-diaminomethylcyclohexane and 3,4-diaminomethylcyclohexane. The proportion of the further isomers of diamino-1-methylcyclohexane is typically 0% to 1% by weight, especially less than 0.5% by weight, based on the MDACH starting mixture.

The term "MDACH" refers to all the isomers of 2,4- and 2,6-MDACH present in the MDACH starting mixture, irrespective of whether they are a cis or trans isomer. The same applies to all the other MDACH-containing mixtures disclosed in the context of this application, especially cis- and trans-enriched MDACH.

MDACH is the reference parameter for specification of the percentages by weight of 2,4- and 2,6-MDACH in the MDACH starting mixture. Consequently, the percentages by weight for 2,4- and 2,6-MDACH always add up to 100% by weight. The same likewise also applies to all the other MDACH-containing mixtures disclosed in the context of this application, especially cis and trans-enriched MDACH.

The MDACH starting mixture is typically prepared by hydrogenating toluene-2,4- or -2,6-diamine or a mixture of toluene-2,4-diamine and toluene-2,6-diamine. By-products that occur here include low boilers, which can be removed for the most part by subsequent distillation. The MDACH starting mixture thus obtained may still comprise small amounts of impurities, especially methylcyclohexylamines (MCHA), but also vicinal diamino-1-methylcyclohexane compounds, for example 2,3-diaminomethylcyclohexane and 3,4-diaminomethylcyclohexane, Typically, the MDACH starting mixture comprises the following isomers:

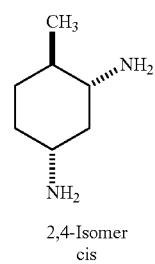

2,4-Isomer
cis

2,6-Isomer
cis

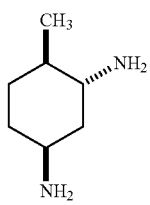

2,4-Isomer
trans

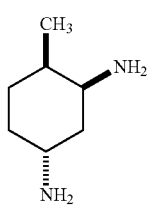

2,4-Isomer
trans

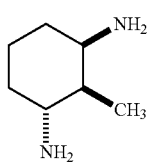

2,6-Isomer
trans

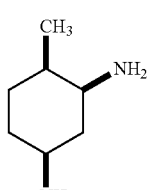

2,4-Isomer
cis

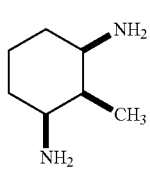

2,6-Isomer
cis

Only diastereomers are shown. Compounds 2 and 7 are meso forms. For all the other compounds, there also exists a corresponding enantiomer in each case, and so there is total of 12 different isomers.

The MDACH starting mixture may comprise, for example, 0% by weight of 2,4-MDACH and 100% by weight of 2,6-MDACH, based in each case on the total amount of MDACH present in the MDACH starting mixture. It may likewise comprise 100% by weight of 2,4-MDACH and 0% by weight of 2,6-MDACH, based in each case on the total amount of MDACH present in the MDACH starting mixture. It nay thus comprise exclusively 2,4-MDACH or 2,6-MDACH. In addition, it may also comprise 2,4- and 2,6-MDACH. This depends essentially on whether toluene-2,4-diamine, toluene-2,6-diamine or a mixture of toluene-2,4-diamine and toluene-2,6-diamine used in the preparation process. In principle, the preparation of the MDACH starting mixture gives rise to both trans and cis isomers. This means that 2,4- and 2,6-MDACH are typically present in both configurations.

If a mixture comprises exclusively 2,4- or 2,6-MDACH, the term "MDACH" necessarily relates only to the corresponding end trans isomers of 2,4- or 2,6-MDACH. If 2,4- and 2,6-MDACH are present, MDACH refers both to the corresponding cis and trans isomers of 2,4-MDACH and those of 2,6-MDACH. The same likewise applies to all the other MDACH-containing mixtures disclosed in the context of this application, especially cis- and trans-enriched MDACH.

The MDACH starting mixture preferably comprises both 2,4- and 2,6-MDACH. More particularly, the MDACH starting mixture comprises 5% to 95% by weight of 2,4-MDACH and 5% to 95% by weight of 2,6-MDACH, based on the total amount of MDACH present in the MDACH starting mixture. More preferably, the MDACH starting mixture comprises 50% to 95% by weight of 2,4-MDACH and 5% to 50% by weight of 2,6-MDACH, based on the total mount of MDACH present in the MDACH starting mixture.

In addition, the MDACH starting mixture may comprise further impurities, for example MCHA. Preferably, the MDACH starting mixture consists to an extent of more than 95% by weight, more preferably to an extent of more than 98% by weight and most preferably to an extent of more than 99% or even 100% by weight of MDACH.

As described above, the MDACH starting mixture comprises both cis and trans isomers. Unless stated otherwise, the terms "cis" and "trans" in each case refer to the positions of the amino groups relative to one another.

The MDACH starting mixture preferably has a proportion of trans isomers of 5% to 60% by weight and a proportion of cis isomers of 40% to 95% by weight, more preferably a proportion of trans isomers of 10% to 55% by weight and a proportion of cis isomers of 45% to 90% by weight, and most preferably a proportion of trans isomers of 20% to 50% by weight and a proportion of cis isomers of 50% to 80% by weight or even a proportion of trans isomers of 35% to 50% by weight and a proportion of cis isomers of 50% to 65% by weight, based in each case on the total amount of MDACH present in the MDACH starting mixture.

The proportion of cis isomers (cis content) and trans isomers (trans content) in the MDACH starting mixture can be calculated by the following formula:

$$cis \text{ content} = \frac{[cis]}{[trans]+[cis]} \cdot 100\% \text{ by weight}$$

$$trans \text{ content} = \frac{[trans]}{[trans]+[cis]} \cdot 100\% \text{ by weight}$$

In this context, cis content+trans content=100% by weight.

The expression [cis] denotes the total mass (=total amount) of the cis isomers present in the MDACH starting mixture, irrespective of whether they are 2,4- or 2,6-MDACH. Correspondingly, the expression [trans] denotes the total mass of the trans isomers present in the MDACH starting mixture, irrespective of whether they are 2,4- or 2,6-MDACH. Consequently, the sum total of [trans]+[cis] denotes the total mass of the MDACH present in the MDACH starting mixture. MDACH serves as a reference parameter for specification of the percentages by weight of the cis and trans isomers in the MDACH starting mixture. Consequently, the percentages by weight for the cis and trans isomers of MDACH always add up to 100% by weight.

The above formulae for calculation of the cis and trans content likewise apply to all the other MDACH-containing mixtures disclosed in the context of this application, especially cis- and trans-enriched MDACH.

In the inventive distillation of the MDACH starting mixture, trans-enriched MDACH is distilled off. As a result, the cis isomer becomes enriched in the bottoms. In addition, the bottom product typically comprises the predominant portion of the auxiliary.

The process of the invention can be conducted either continuously or batchwise.

The inventive distillation of the MDACH starting mixture in the presence of an auxiliary is typically effected with the aid of evaporators and/or columns. Suitable columns for this purpose are know to those skilled in the art.

Preference is given to packed columns having structured packings or random packings, tray columns having trays such as sieve trays, bubble-cap trays or valve trays. Useful evaporators include all the standard variants, for example circulation evaporators, thin-film evaporators and falling-film evaporators. The columns can be designed as conventional columns, as columns with a side draw or as dividing wall columns.

In the case of a continuous mode of operation of the distillation, the column is preferably adjusted so as to result in a reflux ratio (reflux/distillate removal) in the range from a 0.1 to infinity, preferably from 1 to 10, Suitable columns preferably have a number of theoretical plate ($N_{th}$) of 10 to 150, more preferably of 30 to 110.

The distillation method of the invention is preferably conducted at a top temperature of 30 to 280° C. and a top pressure of 1 to 1000 mbar, more preferably at a top temperature of 70 to 220° C. and a top pressure of 5 to 800 mbar and most preferably at a top temperature of 80 to 180° C. and a top pressure of 10 to 500 mbar or even at a top temperature of 80 to 144° C. and a top pressure of 10 to 150 mbar.

Preferably, the inventive distillation is conducted in the absence of oxygen. "Absence" is understood here to mean that the proportion by volume of oxygen is less than 0.1%, especially less than 0.01% and very particularly less than 0.001%, based on the total volume of the distillation column.

The molar ratio of auxiliary and MDACH is preferably greater than 0.2, more preferably 0.3 to and most preferably 0.5 to 2. In the case of the batchwise mode of operation, the MDACH starting mixture and the auxiliary are initially charged in the distillation still in the appropriate ratio. In the case of the continuous reaction regime, the corresponding ratio is established via the feed streams of the MDACH starting mixture and the auxiliary.

Definition of 'molar ratio':(molar amount of the auxiliary)/(molar amount of the total amount of the MDACH present in the MDACH starting mixture).

In the batchwise regime, the MDACH starting mixture and the auxiliary can be initially charged in a distillation still, optionally with an attached column, preferably with exclusion of air, and heated together. During the distillation, individual fractions of the trans-enriched MDACH can be removed.

Preferably, the distillation of the MDACH starting mixture is conducted continuously in the presence of an auxiliary.

More preferably, the process of the invention is conducted continuously and comprises the following steps:
a) feeding the auxiliary into a column (K),
b) feeding the MDACH starting mixture into K,
c) distilling trans-enriched MDACH out of K.

Columns (K) used are preferably the abovementioned column types. K preferably has a number of theoretical plates ($N_{th}$) of 10 to 150, more preferably of 30 to 110.

Typically, the column (K) is equipped with a condenser and an evaporator.

In steps a) and b), the MDACH starting mixture and the auxiliary are fed into K, preferably in the rectifying or tripping section. In this case, they can be fed into K together. Preferably, the MDACH starting mixture and the auxiliary are first mixed and then fed into K.

More preferably, the MDACH starting mixture and the auxiliary are fed into K separately from one another. Most preferably, the auxiliary is fed in above the feed of the MDACH starting mixture. More particularly, the auxiliary is fed in in the upper quarter of the theoretical plates in the column, and the MDACH starting mixture is fed in in the lower quarter of the theoretical plates in the column. Most preferably, the auxiliary is fed in at least 10 or even at least 20 theoretical plates above the feed of the MDACH starting mixture.

The auxiliary and the MDACH starting mixture can be fed in in steps a) and b) In liquid form, in gaseous form, or else in boiling liquid form.

If a column has, for example, 40 theoretical plates, the first 10 theoretical plates, proceeding from the lower end of the column, constitute the first quarter, plates 11 to 20 the second quarter, plates 21 to 30 the third quarter, and plates 31 to 40 the last or upper quarter of the column. The same applies to other divisions of a column, for example thirds (see below).

In step c), trans-enriched MDACH is drawn off, typically at the top of the column as distillate or as a sidestream. If the trans-enriched MDACH is drawn off in a sidestream, the side draw point for removal of the trans-enriched MDACH from K in step c) is preferably at least 1, more preferably at least 5, theoretical plates above the feed point of the auxiliary.

A preferred embodiment of the process of the invention is shown in FIG. 1. The column (K) is equipped with an evaporator and a condenser. The MDACH starting mixture is fed in continuously in the lower third and the auxiliary in the upper third of the theoretical plates of the column (steps a) and b)). The distillate drawn off is trans-enriched MDACH (step c)).

The trans-enriched MDACH may comprise impurities, especially auxiliary and MCHA.

For removal of low boilers, i.e. those compounds having a lower boiling point than MDACH, especially MCHA, it is advantageous to draw off the trans-enriched MDACH in a sidestream while distillate is being drawn off in the top condenser. The latter likewise comprises, as well as MDACH, low boilers (especially MCHA), as a result of which the proportion thereof in the trans-enriched MDACH which is drawn off in the sidestream is reduced.

It is additionally advantageous when the top condenser is followed downstream by a postcondenser. In this case, what is called postcondenser distillate can be drawn off in the postcondenser. The postcondenser distillate comprises, as well as MDACH, low boilers (especially MCHA), as a result of which the proportion thereof in the trans-enriched MDACH which is drawn off in the sidestream is reduced.

More particularly, distillate can be drawn off both in the top condenser and in the postcondenser. This leads to a further reduction in low boilers in the trans-enriched MDACH which is drawn off in the sidestream.

The proportion of auxiliary in the trans-enriched MDACH is typically low when a column with a high separating performance is used and there are a sufficient number of plates between the feed of the auxiliary and the draw of the trans-enriched MDACH (in the distillate and/or side draw). Preferably, there is at least one theoretical plate, more preferably at least 5 theoretical plates, between the feed of the auxiliary and the draw of the trans-enriched MDACH.

A further means of reducing the proportion of auxiliary and MCHA in the trans-enriched MDACH is to conduct a second distillation step.

Preferably, the continuous process of the invention comprises, in addition to steps a) to c), the further steps of:
  d) feeding the trans-enriched MDACH from step c) into a column (K')
  e) removing trans-enriched MDACH from K' in the sidestream or distillate.

In this case, the trans-enriched MDACH obtained in step e) has a lower level of impurities than the trans-enriched MDACH distilled off in step c).

Steps d) to e) can especially be conducted when the trans-MDACH obtained is to be purified further. This is advisable, for example, when the trans-enriched MDACH obtained in step c) comprises more than 0.1% by weight of auxiliary or more than 0.1% by weight of MCHA, based on the total mass of the trans-enriched MDACH.

Columns (K') used are preferably the abovementioned column types. K' preferably has a number of theoretical plates ($N_{th}$) of 10 to 150, more preferably of 30 to 110.

Typically, the column (K') is equipped with a condenser and an evaporator.

Preferably, in step d), the trans-enriched MDACH is fed in in the middle third of the theoretical plates of K'. Most preferably, in the case of side draw removal of the trans-enriched MDACH, the side draw point for removal of the trans-enriched MDACH from K' in step e) is at least 1, especially at least 5, theoretical plates above the feed point of the trans-enriched MDACH from step c).

In step e), trans-enriched MDACH is drawn off either as sidestream or as distillate. Particular preference is given to the removal of trans-enriched MDACH as distillate when the MCHA concentration has already been reduced sufficiently in step c) or MCHA is not present at all in the MDACH starting mixture.

For removal of low boilers, especially MCHA, it is advantageous to draw off distillate in the top condenser. This distillate likewise comprises, as well as MDACH, low boilers (especially MCHA), as a result of which the proportion thereof in the trans-enriched MDACH is reduced.

It is additionally advantageous when the top condenser is followed downstream by a postcondenser. In this case, what is called postcondenser distillate can be drawn off in the postcondenser. The postcondenser distillate comprises, as well as MDACH, low boilers (especially MCHA), as a result of which the proportion thereof in the trans-enriched MDACH is reduced.

Most preferably, distillate is drawn off both in the top condenser and in the postcondenser. This leads to a further reduction in the level of low boilers in the trans-enriched MDACH.

A further particularly preferred embodiment of the process of the invention is shown in FIG. 2. The columns (K and K') have been provided with an evaporator and a top condenser. The top condenser of K' is followed downstream by a postcondenser. The MDACH starting mixture is fed in continuously in the lower third and the auxiliary in the upper third of the theoretical plates of the first column (K) (steps a) and b)). As distillate, trans-enriched MDACH is drawn off (step c)). This distillate is fed to a second column (K') (step d)). In the postcondenser, postcondenser distillate is drawn off, Optionally, distillate can likewise be drawn off in the top condenser. Trans-enriched MDACH is drawn off in the sidestream (step e)).

In an advantageous configuration of the process of the invention, enriched MDACH can be obtained in a downstream distillation step.

Preference is thus given in this context to a process for preparing cis- and trans-enriched MDACH, comprising the following steps:
  I. inventive distillation of an MDACH starting mixture,
  II. distillation of the bottom product obtained in step I, with distillative removal of cis-enriched MDACH,
wherein
  cis-enriched MDACH is a mixture comprising 0% to 100% by weight of 2,4-MDACH and 0% to 100% by weight of 2,6-MDACH, based on the total amount of MDACH present in the mixture, where the proportion of cis isomers in the mixture, based on the total amount of MDACH present in the mixture, is higher than the proportion of cis isomers in the MDACH starting mixture, based on the amount of MDACH present in the MDACH starting mixture.

Step I corresponds to the inventive distillation of an MDACH starting mixture, which is conducted in the presence of an auxiliary, with distillative removal of trans-enriched MDACH.

Steps I and II are typically effected with the aid of evaporators and/or columns. Suitable columns for this purpose are known to those skilled in the art. Preference is given to the abovementioned column types. Suitable columns preferably have a number of theoretical plates ($N_{th}$) of 10 to 150, more preferably of 30 to 110.

In a continuous regime, the columns are preferably adjusted so as to result in a reflux ratio (reflux/distillate removal) in the range from 0.1 to infinity, preferably from 1 to 10.

The distillation in step I is effected as described above. This means that it is preferably conducted at a top temperature of 30 to 280° C. and a top pressure of 1 to 1000 mbar, more preferably at a top temperature of 70 to 220° C. and a top pressure of 5 to 800 mbar and most preferably at a top temperature of 80 to 180° C. and a top pressure of 10 to 500 mbar or even at a top temperature of 80 to 144° C. and a top pressure of 10 to 150 mbar.

The distillation in step H is effected under the same conditions (top pressure and top temperature) as specified above for step I.

Preferably, steps I and II are conducted in the absence of oxygen. "Absence" is understood here to mean that the proportion by volume of oxygen is less than 0.1%, especially less than 0.01% and very particularly less than 0.001% based on the total volume of the distillation column.

The molar ratio of auxiliary and MDACH is preferably greater than 0.2, more preferably 0.3 to 5 and most preferably 0.5 to 2. In the case of the batchwise mode of operation, the MDACH starting mixture and the auxiliary are initially charged in the distillation still in the appropriate ratio. In the case of the continuous reaction regime, the appropriate ratio is established via the feed streams of the MDACH starting mixture and the auxiliary.

In the case of the batchwise regime of step I, the MDACH starting mixture and the auxiliary car be initially charged in a distillation still, optionally with attached column, preferably with exclusion of air, and heated together. During the distillation, individual fractions of the trans-enriched MDACH can be withdrawn.

In a further step (step II), the bottom product obtained in step I can be worked up further. For this purpose, the same apparatus as for step I may be used, meaning that step II is then effected by heating the bottom product obtained in step I in the same apparatus. In principle, the bottom product can alternatively be distilled in another apparatus. In both cases, the bottom product is present in a distillation still, optionally with attached column, preferably with exclusion of air. In this case, cis-enriched MDACH is distilled off.

Additionally preferred is a process or preparing cis- and trans-enriched MDACH, which is conducted continuously as follows:

In step I:
a) feeding the auxiliary into a column (K),
b) feeding the MDACH starting mixture into K,
c) distilling trans-enriched MDACH out of K.

In step II:
a) feeding the bottom product from K into a second column (K2),
b) distilling cis-enriched MDACH out of K2.

Columns K and K2 used are preferably the abovementioned column types. K and K2 preferably have a number of theoretical plates ($N_{th}$) of 10 to 150, more preferably of 30 to 110.

Typically, columns K and K2 are equipped with a condenser and an evaporator.

The distillation in step I corresponds to the above-described continuous distillation of the MDACH starting mixture in steps a) to c). This means that steps a), b) and c) correspond to steps I a), I b) and I c). Consequently, the corresponding explanations and the features specified therefor as preferred, particularly preferred and very particularly preferred likewise relate to step I. More particularly, the trans-enriched MDACH obtained in step I c) can be worked up further in steps d) and e), which should then be referred to as steps I d) and I e.

In step II a), the bottom product is fed in, preferably in the rectifying or stripping section and more preferably in the lower third of the theoretical plates of K2.

The bottom product can be fed in in step II a) in liquid form, in gaseous form or in boiling liquid form.

In step II b), cis-enriched MDACH is typically drawn off as distillate at the top of the column or as a sidestream.

Preferably, in a step III, the bottom product from K2 is recycled into K. More preferably, the bottom product is recycled into K at the same point as the auxiliary (step I a)).

The bottom product from K2 preferably comprises 60% to 100% by weight of auxiliary and 0% to 40% by weight of MDACH, more preferably 70% to 100% by weight of auxiliary and 0% to 30% by weight of MDACH, based on the total mass of the bottom product. Further preferably, the MDACH present in the bottom product consists of cis isomers to an extent of at least 50%, more preferably 60% and most preferably 70% or even >90% by weight.

By virtue of the recycling of the bottom product from K2 into K, the auxiliary is circulated. In that case, it is no longer necessary in principle to supply the system constantly with fresh auxiliary. In this case, the auxiliary is at first fed to the system in the desired amount via step I a). As soon as an equilibrium ha been established in columns K and K2, the feed of fresh auxiliary can either be stopped entirely or at least distinctly reduced.

In order to prevent the enrichment of high-boiling impurities in the recycled bottom product, preferably at least 1% of the bottom product is discharged. In this case, the amount of fresh auxiliary supplied is adjusted so as to balance out the losses that have arisen as a result of the discharge.

A particularly preferred embodiment of the process of the invention is shown in FIG. 3.

The auxiliary is fed in in the upper third and the MDACH starting mixture in the lower third of the theoretical plates of K (steps I a) and I b)). Trans-enriched MDACH is withdrawn as distillate (step I c)). The bottom product from K is fed to a second column (K2) (step II a)). As distillate, cis-enriched MDACH is drawn off from K2 (step II b)). The bottom product from K2 is recycled into K (step III). A portion of the bottom product from K2 is discharged.

With the aid of the distillation process of the invention, it is possible to prepare trans-enriched MDACH.

Trans-enriched MDACH is a mixture comprising 0% to 100% by weight of 2,4-MDACH, and 0% to 100% by weight of 2,6-MDACH, based on the total amount of MDACH present in the mixture, where the proportion of trans isomers in the mixture, based on the total amount of MDACH present in the mixture, is higher than the proportion of trans isomers in the MDACH starting mixture, based on the amount of MDACH present in the MDACH starting mixture.

It is also possible for the trans-enriched MDACH to comprise further isomers of diamino-1-methylcyclohexane, particularly vicinal diamino-1-methylcyclohexane compounds, for example 2,3-diaminomethylcyclohexane and 3,4-diaminomethylcyclohexane. The proportion of the further isomers of diamino-1-methylcyclohexane is typically 0% to 1% by weight, especially less than 0.5% by weight, based on the trans-enriched MDACH.

The above formulae for calculation of the cis content and trans content likewise apply to the trans-enriched MDACH. An increase in the trans content is thus understood to mean that the trans content (calculated by the above formula) for the trans-enriched MDACH is higher than the trans content (calculated by the above formula) for the MDACH starting mixture.

If, for example, the MDACH starting mixture has a content of 35% by weight of trans isomers (and a content of 65% by weight of cis isomers), the proportion of trans isomers in the trans-enriched MDACH is greater than 35% by weight. It is necessarily the case that the proportion of cis isomers in the trans-enriched MDACH is less than 65% by weight.

The trans-enriched MDACH preferably has a proportion of trans isomers of 55% to 100% by weight, more preferably of 62% to 85% by weight and most preferably of 65% to 80% by weight, based in each case on the total amount of MDACH present in the mixture.

The trans-enriched MDACH may comprise impurities, especially MCHA and auxiliary. Preferably, the trans-enriched MDACH consists of MDACH to an extent of more than 95%, more preferably more than 98% and most preferably 99% or even 100% by weight.

Furthermore, the trans-enriched MDACH preferably comprises 5% to 95% by weight of 2,4-MDACH and 5% to 95% by weight of 2,6-MDACH, and more preferably 50% to 95% by weight of 2,4-MDACH and 5% to 50% by weight of 2,6-MDACH, based in each case on the total amount of MDACH present in the mixture.

In addition, the trans-enriched MDACH preferably comprises not more than 1%, more preferably less than 0.8% or even less than 0.7% by weight of MCHA, based on the total amount of the trans-enriched MDACH.

Most preferably, the trans-enriched MDACH is free of MCHA. This is understood to mean that the proportion of MCHA in the trans-enriched MDACH is less than 0.01% by weight, based on the total amount of the trans-enriched MDACH.

The trans-enriched MDACH preferably comprises not more than 1% and more preferably comprises less than 0.1% by weight of auxiliary, based on the total amount of the trans-enriched MDACH.

Most preferably, the trans-enriched MDACH is free of auxiliary. This is understood to mean that the proportion of auxiliary in the trans-enriched MDACH is less than 0.01% by weight, based on the total amount of the trans-enriched MDACH.

In an advantageous configuration of the process of the invention, it is possible to prepare both cis- and trans-enriched MDACH.

Cis-enriched MDACH is a mixture comprising 0% to 100% by weight of 2,4-MDACH and 0% to 100% by weight of 2,6-MDACH, based on the total amount of MDACH present in the mixture, where the proportion of cis isomers in the mixture, based on the total amount of MDACH present in the mixture, is higher than the proportion of cis isomers in the MDACH starting mixture, based on the amount of MDACH present in the MDACH starting mixture.

It is also possible for the cis-enriched MDACH to comprise further isomers of diamino-1-methylcyclohexane, particularly vicinal diamino-1-methylcyclohexane compounds, for example 2,3-diaminomethylcyclohexane and 3,4-diaminomethylcyclohexane. The proportion of the further isomers of diamino-1-methylcyclohexane is typically 0% to 1% by weight, especially less than 0.5% by weight, based on the cis-enriched MDACH.

The above formulae for calculation of the cis content and trans content in the MDACH starting mixture likewise apply to the cis-enriched MDACH. An increase in the cis content is thus understood to mean that the cis content (calculated by the above formula) for the cis-enriched MDACH is higher than the cis content (calculated by the above formula) for the MDACH starting mixture.

If, for example, the MDACH starting mixture has a content of 65% by weight of cis isomers (and a content of 35% by weight of trans isomers), the proportion of cis isomers in the cis-enriched MDACH is greater than 65% by weight. It is necessarily the case that the proportion of trans isomers in the cis-enriched MDACH is less than 35% by weight.

The cis-enriched MDACH preferably has a proportion of cis isomers of 55% to 100% by weight, based on the total amount of MDACH present in the mixture. A proportion of cis isomers of 60% to 99% by weight or 70% to 95% by weight is likewise preferred, based in each case on the total amount of MDACH present in the mixture.

The cis-enriched MDACH may comprise impurities, especially auxiliary. Preferably, the cis-enriched MDACH consists of MDACH to an extent of more than 95%, more preferably more than 98% and most preferably 99% or even 100% by weight.

Furthermore, the cis-enriched MDACH preferably comprises 5% to 95% by weight of 2,4-MDACH and 5% to 95% by weight of 2,6-MDACH, and more preferably 50% to 100% by weight of 2,4-MDACH and 0% to 50% by weight of 2,6-MDACH, based in each case on the total amount of MDACH present in the mixture.

The cis-enriched MDACH comprises preferably at most 10% and more preferably less than 5% by weight of auxiliary, based on the total amount of the cis-enriched MDACH.

Most preferably, the cis-enriched MDACH is free of auxiliary. This is understood to mean that the proportion of auxiliary in the cis-enriched MDACH is less than 0.01% by weight, based on the total amount of the cis-enriched MDACH.

The present invention further relates to trans-enriched MDACH preparable by the process of the invention. The features emphasized above as preferred, particularly preferred and very particularly preferred for the process of the invention likewise relate to the trans-enriched MDACH preparable by this process.

More particularly, the present invention relates to trans-enriched MDACH, which is a mixture comprising 0% to 100% by weight of 2,4-MDACH and 0% to 100% by weight of 2,6-MDACH, based on the total amount of MDACH present in the mixture, and which has a proportion of trans isomers of 55% to 100% by weight, based on the total amount of MDACH present in the mixture.

It is also possible for the trans-enriched MDACH to comprise further isomers of diamino-1-methylcyclohexane, particularly vicinal diamino-1-methylcyclohexane compounds, for example 2,3-diaminomethylcyclohexane and 3,4-diaminomethylcyclohexane. The proportion of the further isomers of diamino-1-methylcyclohexane is typically 0% to 1% by weight, especially less than 0.5% by weight, based on the trans-enriched MDACH.

More preferably, the trans-enriched MDACH has a proportion of trans isomers of 62% to 85% by weight and most preferably 65% to 80% by weight, based in each case on the total amount of MDACH present in the mixture.

The trans-enriched MDACH preferably consists of MDACH to an extent of more than 95%, more preferably more than 98% and most preferably 99% or even 100% by weight.

Furthermore, the trans-enriched MDACH preferably comprises 5% to 95% by weight of 2,4-MDACH and 5% to 95% by weight of 2,6-MDACH, and more preferably 50% to 95% by weight of 2,4-MDACH and 5% to 50% by weight of 2,6-MDACH, based on the total amount of MDACH present in the mixture.

The trans-enriched MDACH preferably comprises not more than 1%, more preferably less than 0.8% and most preferably less than 0.7% by weight of MCHA, based on the total amount of the trans-enriched MDACH.

The trans-enriched MDACH comprises preferably not more than 1% and more preferably less than 0.1% by weight of auxiliary, based on the total amount of the trans-enriched MDACH.

Most preferably, the trans-enriched MDACH is free of auxiliary. This is understood to mean that the proportion of auxiliary in the trans-enriched MDACH comprises less than 0.01% by weight, based on the total amount of the trans-enriched MDACH.

The present invention further relates to cis-enriched MDACH preparable by the process of the invention. The features emphasized above as preferred, particularly preferred and very particularly preferred for the process of the invention likewise relate to the cis-enriched MDACH preparable by this process.

It is also possible for the cis-enriched MDACH to comprise further isomers of diamino-1-methylcyclohexane, particularly vicinal diamino-1-methylcyclohexane compounds, for example 2,3-diaminomethylcyclohexane and 3,4-diaminomethylcyclohexane. The proportion of the further isomers of diamino-1-methylcyclohexane is typically 0% to 1% by weight, especially less than 0.5% by weight, based on the cis-enriched MDACH.

More particularly, the present invention relates to cis-enriched MDACH, which is a mixture comprising 0% to 100% by weight of 2,4-MDACH and 0% to 100% by weight of 2,6-MDACH, based on the total amount of MDACH present in the mixture, and which has a proportion of cis isomers of 55% to 100% by weight, based on the total amount of MDACH present in the mixture.

The cis-enriched MDACH more preferably has a proportion of cis isomers of 60% to 99% and most preferably 70% to 95% by weight, based in each case on the total amount of MDACH present in the mixture.

Preferably, the cis-enriched MDACH consists of MDACH to an extent of more than 95%, more preferably more than 98% and most preferably 99% or even 100% by weight.

Furthermore, the cis-enriched MDACH preferably comprises 5% to 95% by weight of 2,4-MDACH and 5% to 95% by weight of 2,6-MDACH, and more preferably 50% to 100% by weight of 2,4-MDACH and 0% to 50% by weight of 2,6-MDACH, based in each case on the total amount of MDACH present in the mixture.

The cis-enriched MDACH comprises preferably not more than 10% and more preferably less than 5% by weight of auxiliary, based on the total amount of the cis-enriched MDACH. Most preferably, the cis-enriched MDACH is free of auxiliary. This is understood to mean that the proportion of auxiliary in the cis-enriched MDACH is less than 0.01% by weight, based on the total amount of the cis-enriched MDACH.

All MDACH-containing mixtures, especially the MDACH starting mixture and trans- and cis-enriched MDACH are analyzed with the aid of gas chromatography (GC). For this purpose, the mixture is dissolved in dioxane. This solution is injected into the gas chromatograph with the aid of a syringe. The gas chromatograph is equipped with a column of length 30 m, having an internal diameter of 0.25 m and a film thickness of 0.5 µm. The column itself comprises, as stationary phase, 35% by weight of diphenylpolysiloxane and 65% by weight of dimethylpolysiloxane (RTX35-Amine column from Resteck Corporation). The carrier gas or mobile phase used is helium. The flow rate of the helium is set to 40 mL/min, so as to give a constant flow rate of 1 mL/min of He through the column with the split ratio (division ratio) set to 40:1, For determination of the substances to be analyzed, the gas chromatograph has a flame ionization detector which is operated at 280° C., The column on the gas chromatograph is operated at a temperature in the range from 100 to 250° C.

In order to be able to determine the area percentages and percentages by weight of the peaks to be determined, a defined amount of a standard (dodecane) is added to the mixture dissolved in dioxane. The mixture thus obtained injected into the column with an injection temperature of 100° C. and an inlet pressure of 1 bar. At first, a heating rate of 1° C./min is set, which is maintained until a temperature for the column of 120° C. has been attained. As soon as this temperature has been attained, the heating rate of the column is switched to 5° C./min and maintained until the end temperature of 250° C., Subsequently, the column temperature is held at 250° C. for 10 min.

The process of the invention is elucidated in detail in the examples which follow. The analysis data reported are based on gas chromatography analysis, as described above.

EXAMPLES

Unless stated otherwise, in all the examples, Baxxodur ECX210 was used as MDACH starting mixture.
Composition of Baxxodur ECX 210:
trans isomer: 36% to 38% by weight
2,4 MDACH: 80% to 90% by weight
2,6-MDACH: 10% to 20% by weight
The figures given are each based on the total amount of MDACH present in the MDACH starting mixture.

The MDACH starting mixture consisted to an extent of ≥98% by weight of MDACH.

Example 1

Batch Distillation with Auxiliary (in Accordance with the Invention) and without Auxiliary (not in Accordance with the Invention)

A 1.6 liter Miniplant reactor provided with an anchor stirrer and thermostat was initially charged with 800 g of Baxxodur ECX210 (MDACH starting mixture) and the particular auxiliary with exclusion of air, with a molar ratio of the auxiliary and the molar amount of all the isomers of 2,4-diamino-1-methylcyclohexane and 2,6-diamino-1-methylcyclohexane of 1. The distillation as effected with the aid of a column (Sulzer DX packing, $N_{th}$=30-45) with a reflux divider at top pressure about 20 mbar and a reflux ratio of 1, During the distillation, a fraction of 100 mL was removed and then analyzed by means of GC.

TABLE 1

Proportion of trans isomers as a function of the auxiliary used. All figures are in % by weight and relate to the total amount of MDACH present in the MDACH starting mixture or in the fraction.

| Auxiliary | Fraction |
|---|---|
| No auxiliary | 44.15 |
| Glycerol | 46.03 |
| Propane-1,3-diol | 49.29 |
| Triethanolamine | 46.01 |
| Triethylene glycol | 45.39 |
| Diglycerol | 45.03 |
| Butane-1,4-diol | 46.20 |
| N-(2-Hydroxy-ethyl)aniline | 45.82 |
| cis Butene-1,4-diol | 47.22 |
| Pentane-1,5-diol | 47.09 |
| N-Methyldiethanol-amine | 46.07 |
| 4-(2-Hydroxyethyl)-morpholine | 46.86 |

The results show that the use of an auxiliary leads to an improvement in the separation efficiency with respect to the trans isomers. Propane-1,3-diol has the highest separation efficiency.

Example 2

Batch Distillation with Sulfolane as Auxiliary (not in Accordance with the Invention)

The MDACH starting mixture used was Baxxodur ECX 210 and the auxiliary sulfolane. The experimental setup and experimental procedure correspond to those from example 1, with the difference that the top pressure during the distillation was about 50 mbar During the distillation, a fraction of 100 mL was removed and then analyzed by means of GC.

TABLE 2

Proportion of trans isomers as a function of the use of the sulfolane auxiliary. All figures are in % by weight and are based on the total amount of MDACH present in the MDACH starting mixture or in the fraction.

| Auxiliary | Fraction |
|---|---|
| Without sulfolane | 46.61 |
| With sulfolane | 45.90 |

The results show that an addition of sulfolane as auxiliary does not achieve any significant improvement in the distillation yield of trans isomers, but a deterioration compared to the distillation without sulfolane occurs.

Example 3

Batch Distillation with Propane-1,3-Diol with Different Composition of the MDACH Starting Mixture (in Accordance with the Invention)

The distillation was effected with the aid of a column (Sulzer DX packing+Moritz A3-1000, $N_{th}$ about 60) at a top pressure of 50 mbar. The total amount of MDACH starting mixture and propane-1,3-diol used was about 1000-1200 g, with use in experiment a) of Baxxodur ECX 210 and in experiment b) of a mixture having a proportion of about 44% by weight of trans isomers. The molar ratio of the propane-1,3-diol (auxiliary) and MDACH was 1, The reflux ratio was set to 2. For the rest, the experimental setup and experimental procedure corresponded to those from example 1. During the distillation, a fraction of 100 mL was removed and then analyzed by means of GC.

TABLE 3

Proportion of trans isomers as a function of the proportion of trans isomers in the MDACH starting mixture. All figures are in % by weight and relate to the total amount of MDACH present in the MDACH starting mixture or in the fraction.

| Experiment | Fraction |
|---|---|
| a) | 52.66 |
| b) | 68.91 |

Example 4

Continuous Distillation with Propane-1,3-Diol as Auxiliary (in Accordance with the Invention)

The columns used (Sulzer CY packing, about $N_{th}$=45) have each been equipped with a thin-film evaporator and a separate condenser. The feeds to and draws from the column are shown in schematic form in FIG. 1 for example 4.1 and FIG. 2 for example 4.2. The auxiliary used was propane-1,3-diol and the MDACH starting mixture Baxxodur ECX 210.

Example 4.1

Propane-1,3-diol was fed in in the rectifying section of the column at a pressure of about 50 mbar. The MDACH starting mixture was fed in in the stripping section of the column at a pressure of about 53 mbar. The feeds were boiling liquids.

Variant 1:
Feedrates:
MDACH starting mixture=1540 g/h,
Propane-1,3-diol=920 g/h
Draws:
Distillate=300 g/h
Reflux: 2000 g/h
Results (variant 1):
The trans-enriched MDACH obtained as distillate had the following composition:
trans isomer: about 66% by weight
2,4-MDACH: about 68% to 69% by weight
2,6-MDACH: about 31% to 32% by weight
The figures are each based on the total amount of MDACH present in the distillate.
MCHA was present in the distillate to an extent of about 1 GC area % (GC area percent). The propane-1,3-diol was present almost entirely in the bottoms.

Variant 2:
Feed rates:
MDACH starting mixture=1540 g/h,
Propane-1,3-diol=1250 g/h
Draws:
Distillate=300 g/h
Reflux: 1700 to 1800 g/h
Results (variant 2):
The trans-enriched MDACH obtained as distillate had the following composition:
trans isomer: about 74% by weight
2,4-MDACH: about 64% by weight
2,6-MDACH: about 36% by weight
The figures are each based on the total amount of MDACH present in the distillate.
MCHA was present in the distillate to an extent of about 1 GC area %, The proportion of propane-1,3-diol in the distillate was about 13.8% by weight, based on the total amount of the distillate.

Example 4.2

Feeds to and draws from the columns are shown schematically in FIG. 2.
The first distillation step (DISTILLATION 1) corresponds to variant 2 for example 4.1. The feed composition for DISTILLATION 2 thus corresponds to the composition of the distillate obtained in variant 2 of example 4.1.
The figures which follow in relation to variants 1 and 2 relate to the second distillation step (DISTILLATION 2).

Variant 1
Feed rate: 1000 g/h
Draws:
Sidestream=590 g/h,
Distillate (in the top condenser)=0 g/h,
Postcondenser=about 10 to 30 g/h
Reflux (column)=2000 g/h
Temperatures:
Top condenser=85° C.,
Postcondenser=about 15° C.
Results (variant 1):
The trans-enriched MDACH obtained in the sidestream had the following composition:
trans isomer: about 74% by weight
2,4-MDACH: about 60% by weight
2,6-MDACH: about 40% by weight The figures are each based on the total amount of MDACH present in the sidestream.

The propane-3-diol was present almost entirely in the bottoms. The MCHA content in the sidestream was reduced by the postcondenser at the top of the column from about 1 GC area % in the feed composition to about 0.61-0.66 GC area %.

Variant 2:
Feed rate: 1000 g/h
Draws
Sidestream=490 g/h,
Distillate (in top condenser)=100 g/h,
Postcondenser=about 10-30 g/h
Reflux (column)=2000 g/h
Temperatures:
Top condenser=90° C.,
Postcondenser=about 15° C.
Results (variant 2):
The trans-enriched MDACH present in the sidestream had the following composition:
trans isomer; about 74% by weight
2,4-MDACH: about 60% by weight
2,6-MDACH: about 40% by weight
The figures are each based on the total amount of MDACH present in the sidestream.

The propane-1,3-diol was present almost entirely in the bottoms. The MCHA content in the sidestream was reduced by the postcondenser at the top of the column and the distillate draw in the top condenser from about 1% in the feed composition to about 0.57 GC area %.

Preparation of Cis-Enriched MDACH and Recovery of the Auxiliary (in Accordance with the Invention):

The bottom product from example 4.1 variant 1, was initially charged in a distillation still equipped with a column (Sulzer DX packing+Moritz A3-1000, $N_{th}$=about 60) and distilled at a top pressure of about 250 mbar with exclusion of air. This gave a bottom product which consisted to an extent of about 65% by weight of propane-1,3-diol. This can be used again in the distillation of the MDACH starting mixture. The distillate obtained was a mixture which had the following composition:
cis isomer: about 83% by weight
2,4-MDACH: about 92% by weight
2,6-MDACH: about 8% by weight
The figures are each based on the total amount of MDACH present in the distillate.

The invention claimed is:

1. A process for preparing trans-enriched MDACH, the process comprising:
distilling an MDACH starting mixture in the presence of an auxiliary, wherein trans-enriched MDACH is distilled off,
and wherein
the auxiliary is an organic compound having
a molar mass of 62 to 500 g/mol,
a boiling point at least 5° C. above the boiling point of cis,cis-2,6-diamino-1-methylcyclohexane, where the boiling points are each based on a pressure of 50 mbar, and
2 to 4 functional groups selected independently from the group consisting of an alcohol group, a primary amino group, a secondary amino group and a tertiary amino group,
wherein the MDACH starting mixture comprises a total amount of MDACH, wherein the total amount of MDACH in the MDACH starting mixture comprises 0% to 100% by weight of 2,4-diamino-1-methylcyclohexane (2,4-MDACH) and 0% to 100% by weight of 2,6-diamino-1-methylcyclohexane (2,6-MDACH), and wherein the MDACH starting mixture comprises both trans and cis isomers, and
wherein trans-enriched MDACH is a mixture comprising a total amount of MDACH, wherein the total amount of MDACH in the mixture of trans-enriched MDACH comprises 0% to 100% by weight of 2,4-MDACH and 0% to 100% by weight of 2,6-MDACH, where the proportion of trans isomers in the total amount of MDACH in the mixture of trans-enriched MDACH is higher than the proportion of trans isomers in the total amount of MDACH in the MDACH starting mixture.

2. The process according to claim 1, which is performed continuously and comprises:
feeding the auxiliary into a column,
feeding the MDACH starting mixture into the column, and
distilling trans-enriched MDACH out of the column.

3. The process according to claim 2, wherein the auxiliary is fed in above the feed of the MDACH starting mixture.

4. The process according to claim 1, wherein the distillation of the MDACH starting mixture in the presence of the auxiliary is conducted at a top temperature of 80 to 180° C. and a top pressure of 10 to 500 mbar.

5. The process according to claim 1, wherein the auxiliary has either
2 to 4 alcohol groups,
a primary, secondary or tertiary amino group and 1 to 3 alcohol group(s), or
2 to 4 functional groups selected independently from the group consisting of a primary amino group, a secondary amino group and a tertiary amino group.

6. The process according to claim 1, wherein the auxiliary, has, in addition to the 2 to 4 functional groups, either no further heteroatoms or 1 to 3 ether group(s) and otherwise no further heteroatoms.

7. The process according to claim 1, wherein the auxiliary has a molar mass of from 76 to 300 g/mol.

8. The process according to claim 1, wherein the auxiliary has
a molar mass of 62 to 250 g/mol,
a melting point of less than 60° C. at a pressure of 1 bar, and
2 to 4 alcohol groups,
where the auxiliary has, in addition to the 2 to 4 alcohol groups, either no further heteroatoms or 1 or 2 ether group(s) and otherwise no further heteroatoms.

9. The process according to claim 1, wherein the auxiliary has
a molar mass of 75 to 300 g/mol
a melting point of less than 60° C. at a pressure of 1 bar, and
a primary, secondary or tertiary amino group and to 3 alcohol group(s),
where the auxiliary has, in addition to the primary, secondary or tertiary amino group and 1 to 3 alcohol group(s), either no further heteroatoms or 1 ether group and otherwise no further heteroatoms.

10. The process according to claim 1, wherein the auxiliary has
a molar mass of 100 to 300 g/mol,
a melting point of less than 60° C. at a pressure of 1 bar, and
2 to 4 functional groups selected independently from the group consisting of a primary amino group, a secondary amino group and a tertiary amino group, where the auxiliary has, aside from the 2 to 4 functional groups, no further heteroatoms.

11. The process according to claim 1, wherein the auxiliary is at least one selected from the group consisting of: 2-methylpropane-1,3-diol, hexane-1,2-diol, cis-cyclopentane-1,2-diol, trans-cyclopentane-1,2-diol, propane-1,3-diol, pentane-1,5-diol, 2-methylpropane-1,3-diol, hexane-1,3-diol, hexane-2,4-diol, cyclobutane-1,3-diol, cyclopentane-1,3-diol, cyclohexane-1,3-diol, cis- and trans-butene-1,4-diol, butane-1,4-diol, 2,3-dimethylbutane-1,4-diol, 2,2-dimethylbutane-1,4-diol, pentane-1,4-diol, 2,3-dimethylpentane-1,5-diol, hexane-1,4-diol, hexane-1,3,6-triol, hexane-1,2,6-triol, glycerol, diglycerol, diethylene glycol, triethylene glycol, dipropylene glycol, diethanolamine, N-methyldiethanolamine, N-propyldiethanolamine, N-butyldiethanolamine, triethanolamine, N-ethylpropanolamine, N-propylethanolamine, N,N-dipropylethanolamine, N,N-dibutylethanolamine, dipropanolamine, N-methyldipropanolamine, N-propyldipropanolamine, N-butyldipropanolamine, tripropanolamine, diisopropanolamine, N-methyldiisopropanolamine, triisopropanolamine, N-2-methylaminopropanol, 4-(2-hydroxyethyl)morpholine, pentanolamine, hydroxyethylpiperazine, N-(2-hydroxyethyl)aniline, N,N-di(2-hydroxyethyl)aniline, 3-(cyclohexylamino)propylamine, dipropylenetriamine, triethylenetetramine, 3-(2-aminoethylamino)propylamine, and isophoronediamine.

12. The process according to claim 1, wherein the auxiliary is at least one selected from the group consisting of: glycerol, propane-1,3-diol, cis-butene-1,4-diol, triethylene glycol, diglycerol, 3-(cyclohexylamino)propylamine, 4-(2-hydroxyethyl)morpholine, N-(2-hydroxyethyl)aniline, triethanolamine, and N-methyldiethanolamine.

13. The process according to claim 1, wherein the MDACH starting mixture comprises more than 95% by weight of MDACH.

14. The process according to claim 1, wherein the total amount of MDACH in the MDACH starting mixture comprises 5% to 95% by weight of 2,4-MDACH and 5% to 95% by weight of 2,6-MDACH.

15. The process according to claim 1, wherein the total amount of MDACH in the MDACH starting mixture comprises 5% to 60% by weight of trans isomers and 40% to 95% by weight of cis isomers.

16. The process according to claim 1, wherein the total amount of MDACH in the mixture of trans-enriched MDACH comprises 55% to 100% by weight of trans isomers.

17. The process according to claim 1, wherein the trans-enriched MDACH comprises more than 95% by weight of MDACH.

18. The process according to claim 1, wherein the total amount of MDACH in mixture of trans-enriched MDACH comprises 5% to 95% by weight of 2,4-MDACH and 5% to 95% by weight of 2,6-MDACH.

19. A process for preparing cis- and trans-enriched MDACH, the process comprising:

I. preparing trans-enriched MDACH by the process according to claim 1; and

II. distilling the bottom product obtained in preparing I, with distillative removal of cis-enriched MDACH, wherein cis-enriched MDACH is a mixture comprising a total amount of MDACH, wherein the total amount of MDACH in the mixture of cis-enriched MDACH comprises 0% to 100% by weight of 2,4-MDACH and 0% to 100% by weight of 2,6-MDACH, where the proportion of cis isomers in the total amount of MDACH in the mixture of cis-enriched MDACH is higher than the proportion of cis isomers in the total amount of MDACH in the MDACH starting mixture.

20. The process according to claim 19, which is performed continuously, wherein:

the preparing I comprises:
   feeding the auxiliary into a column,
   feeding the MDACH starting mixture into the column, and
   distilling trans-enriched MDACH out of the column, and the distilling II comprises:
   feeding the bottom product from the column into a second column, and
   distilling cis-enriched MDACH out of the second column.

21. The process according to claim 20, farther comprising:

III. recycling the bottom product from the second column into the column of the preparing I.

22. The process according to claim 19, wherein the total amount of MDACH in the mixture of cis-enriched MDACH comprises 55% to 100% by weight of cis isomers.

23. The process according to claim 19, wherein the cis-enriched MDACH comprises more than 95% by weight of MDACH.

24. The process according to claim 19, wherein the total amount of MDACH in the mixture of cis-enriched MDACH comprises 5% to 95% by weight of 2,4-MDACH and 5% to 95% by weight of 2,6-MDACH.

25. Trans-enriched MDACH, comprising a total amount of MDACH comprising:
   0% to 100% by weight of 2,4-MDACH; and
   0% to 100% by weight of 2,6-MDACH,
   with the proviso that 2,4-MDACH or 2,6-MDACH is present,
   wherein a proportion of trans isomers present in the total amount of MDACH is from 62% to 85% by weight.

26. Cis-enriched MDACH, comprising a total amount of MDACH comprising:
   0% to 100% by weight of 2,4-MDACH; and
   0% to 100% by weight of 2,6-MDACH,
   with the proviso that 2,4-MDACH or 2,6-MDACH is present,
   wherein a proportion of cis isomers present in the total amount of MDACH is from 70% to 95% by weight.

* * * * *